United States Patent [19]

Mori et al.

[11] Patent Number: 5,087,762

[45] Date of Patent: Feb. 11, 1992

[54] PROCESS FOR PRODUCING VITAMIN A ALDEHYDE

[75] Inventors: Toshiki Mori; Takashi Onishi; Kazuo Yamamoto, all of Kurashiki, Japan

[73] Assignee: Kuraray Company Ltd., Kurashiki, Japan

[21] Appl. No.: 618,922

[22] Filed: Nov. 28, 1990

[30] Foreign Application Priority Data

Jan. 8, 1990 [JP] Japan .................................. 2-1948

[51] Int. Cl.$^5$ ........................ C07C 45/61; C07C 47/42
[52] U.S. Cl. ................................................... 568/447
[58] Field of Search ................... 568/378, 470, 447; 560/260

[56] References Cited

U.S. PATENT DOCUMENTS

| | | | |
|---|---|---|---|
| 2,819,311 | 1/1958 | Klein et al. | 568/447 |
| 3,060,229 | 10/1962 | Eiter et al | 560/260 |
| 4,148,829 | 4/1979 | Olson et al. | 568/447 |

FOREIGN PATENT DOCUMENTS 2556161 12/1976 Fed. Rep. of Germany .

861460 2/1961 United Kingdom ................ 568/447

OTHER PUBLICATIONS

Research Disclosure, Dec. 1983, p. 375; Abstract No. 23618, "Verfahren zur Oxidation von primaren Alkoholen".

*Primary Examiner*—Werren B. Lone
*Attorney, Agent, or Firm*—Oblon, Spivak, McClelland, Maier & Neustadt

[57] ABSTRACT

The invention provide a process for producing vitamin A aldehyde in high yield by oxidizing vitamin A with a aldehyde of the general formula (1)

$$R_2-\underset{\underset{R_3}{|}}{\overset{\overset{R_1}{|}}{C}}-CHO \qquad (1)$$

wherein $R_1$, $R_2$ and $R_3$ are the same or different and respectively represents a lower alkyl group or a lower alkenyl group in the presence of aluminum alkoxide in a catalytic amount.

6 Claims, No Drawings

PROCESS FOR PRODUCING VITAMIN A ALDEHYDE

BACKGROUND OF THE INVENTION

1. Field of the Invention

This invention relates to a process for producing vitamin A aldehyde (retinal).

Vitamin A aldehyde is not only a valuable biologically active substance as itself but also a useful starting material for producing carotene.

2. Description of the Prior Art

As a simple and easy production process of vitamin A aldehyde, there is known a process oxidizing vitamin A obtained by the hydrolysis of commercially available vitamin A acetate. However, vitamin A or vitamin A aldehyde is thermally unstable because they have not only a number of double bonds sensitive to oxidation but also highly reactive allyl alcohol or $\alpha,\beta$-unsaturated aldehyde structures, and further they must be handled under a condition cut off light and oxygen.

Accordingly the oxidation of vitamin A and vitamin A aldehyde must be carried out under a mild condition. Also the reaction products tend to decompose under a severe condition of after treatment resulting in a poor yield of objective material. Further, vitamin A has all double bonds in trans form, so that it is required to be transformed into vitamin A aldehyde having all double bonds in trans form unchanged without isomerization.

Under these restricted oxidation conditions, several methods have been disclosed as described below. For example:

(1) An oxidizing method using manganese dioxide (R. A. Morton et. al., Biochem. J., 42, 516 (1948)) or nickel peroxide (Ger. Offen. 2,415,928 (1973))

(2) An oxidizing method by oxygen in the presence of platinum catalyst (Karrer, et. al., Helv. Chim. Acta 40, 265 (1957))

(3) An oxidizing method by oxygen in the presence of 4-oxo-2,2,6,6-tetramethylpiperidine-1-oxyl and copper chloride catalyst (Japanese Patent Application Laid-open No. 63-233943)

(4) An oxidizing method by acetaldehyde in benzene in the presence of aluminum isopropoxide Al-[OCH(CH$_3$)$_2$]$_3$ (Hawkins, et. al., J. Chem. Soc., 411 (1944)).

These prior art methods have the following problems. The method (1) requires a large excess amount of solid metal oxide relative to vitamin A. And also the yield by the method (1) depends on the activity of the metal oxide. The method (2) requires an expensive platinum catalyst, and also has a lower yield. The method (3) requires expensive 4-oxo-2,2,6,6-tetramethylpiperidine-1-oxyl as a catalyst and also a solvent having a higher boiling point such as N,N-dimethylformamide. The method (4) requires a severe reaction condition resulting in a lower yield.

An object of the invention is to provide a process for producing vitamin A aldehyde from vitamin A economically and in high yield without isomerization.

SUMMARY OF THE INVENTION

According to the invention the aforementioned object can be accomplished by a process comprising the reaction of vitamin A with the aldehydes of the general formula (1)

wherein $R_1$, $R_2$ and $R_3$ are the same or different and respectively represents a lower alkyl group or a lower alkenyl group in the presence of catalytic amount of aluminum alkoxide.

DESCRIPTION OF THE PREFERRED EMBODIMENT $R_1$, $R_2$ and $R_3$ in the general formula (1) are described in detail. $R_1$, $R_2$ and $R_3$ of the general formula (1) respectively represents a lower alkyl or a lower alkenyl group. Examples of the lower alkyl group include $C_{1-4}$ alkyl groups such as a methyl group, an ethyl group, a n-propyl group, an i-propyl group, a n-butyl group, a sec-butyl group, a t-butyl group and the like. Examples of the lower alkenyl group include $C_{2-5}$ alkenyl groups such as a vinyl group, an allyl group, a 2-methyl-2-propenyl group, a 3-methyl-3-butenyl group, a 3-methyl-2-butenyl group, an allenyl group and the like. Further $R_1$, $R_2$ and $R_3$ respectively are different or two or three of them are the same.

Examples of the aldehyde of the general formula (1) include trimethylacetaldehyde, 2,2-dimethylbutanal, 2-ethyl-2-methylbutanal, 2,2-dimethyl-4-pentenal, 2,2-dimethylpentanal, 2,2-dimethylpenta-3,4-dienal and the like. Particularly, trimethylacetaldehyde (boiling point 74° C. at 730 mmHg) and 2,2-dimethy-4-pentenal (boiling point 124° C. at 760 mmHg) are preferable examples of the invention because the both substances themselves and the corresponding alcohols formed at the preparation of vitamin A aldehyde as side products have lower boiling points, so that these materials can be easily removed from the reaction mixtures at lower temperatures after the completion of the reaction.

The amount of the aldehyde of the general formula (1) is one or more equivalents relative to the amount of vitamin A to be oxidized, but preferably in the range of from 1.1 to 3 equivalents for efficiently and economically carrying out of the reaction.

Examples of aluminum alkoxides used as the catalyst of the reaction includes aluminum isopropoxide, aluminum tert-butoxide, aluminm sec-butoxide, aluminum phenoxide and the like, however, aluminum isopropoxide is preferably used from the standpoint of versatility and economy.

The amount of aluminum catalyst to be used is in the range of from 0.1 to 30 mole percent relative to vitamin A to be oxidized, however, normally an amount of the catalyst in the range of from 2 to 10 mole percent is used.

Besides, water contamination in the reaction system degrades the catalytic activity of aluminum alkoxide and tends to stop the reaction, so that the water contamination must be carefully avoided.

The reaction is carried out at a temperature ranging from 10° C. to 80° C. depending on the reaction period, however, preferably ranging from 20° C. to 50° C. considering the stability of formed vitamin A aldehyde.

For the present reaction, the use of a solvent is not necessarily required. But if the aluminum alkoxide as the catalyst hardly dissolves in the reaction mixture, a solvent selected from the group consisting of hydrocarbon type solvents such as toluene, hexane, etc., halogenated hydrocarbon type solvents such as methylene chloride, chloroform, etc., ether type solvents such as tetrahydrofuran, diethyl ether, etc., and ester type solvents such as ethyl acetate, etc. can be used.

The reaction period of the reaction is normally in the range of from 10 min. to 2 hours depending on the amount of catalyst used and the reaction temperature.

Stopping of the reaction is accomplished by the addition of water, aqueous hydrochloric acid solution, aqueous sulfuric acid solution and the like. After the addition of small amount of water for stopping the reaction, the aldehyde of the general formula (1) used for the reaction and the alcohol formed as a reaction byproduct are distilled off from the reaction mixture under a reduced pressure, followed by the purification and separation directly from the residue by means of column chromatography or recrystallization to obtain the objective vitamin A aldehyde easily.

Also, after the completion of the reaction, the reaction mixture is extracted by an organic solvent such as toluene, hexane, diethyl ether, methylene chloride, ethyl acetate or the like, and subjected to separation. After the separated organic layer is washed with water, aqueous sodium carbonate solution and the like, the organic solvent is removed and thereafter subjected to column chromatography or recrystallization for the separation and purification to obtain the objective vitamin A aldehyde.

The present invention is more particularly described by way of examples, which should not be construed as limiting the invention.

EXAMPLE 1

Synthesis of Vitamin A Aldehyde using Trimethylacetaldehyde (1) Purification by Column Chromatography After the reaction of 11.6 g (33.67 mmol) of vitamin A acetate (purity 95.2%) with 5.6 g of an aqueous 50% sodium hydroxide solution in 80 g of methanol at room temperature for 1 hour, hexane and water were added to the reaction mixture and the organic layer was separated. After the obtained organic layer was washed with water, the organic solvent was removed by distillation under a reduced pressure to obtain 9.85 g of crude vitamin A.

To the obtained crude vitamin A, 6.08 g (16.7 mmol) of trimethylacetaldehyde and 360 mg (1.75 mmol) of aluminum isopropoxide were added, and the reaction mixture was agitated at 45°-50° C. for 45 min. After the stopping of reaction by the addition of 0.15 ml of water, unreacted trimethylacetaldehyde and neopentyl alcohol formed as a reaction by-product were removed by distillation under a reduced pressure (50° C., 10 mmHg) to obtain 11.3 g of crude vitamin A aldehyde.

The obtained crude vitamin A aldehyde was purified by column chromatography (eluent: hexane/ethyl acetate=85/15) to obtain 7.68 g of purified vitamin A aldehyde (yield 80%, total trans form ratio 98%, melting point 60°-62° C.).

(2) Purification by Recrystallization

After 2.8 g (8.37 mmol) of vitamin A acetate and 1.2 g of an aqueous 50% sodium hydroxide solution were reacted in 15 g of methanol at room temperature for 1 hour, hexane and water were added and separated. After the obtained organic layer was washed with water, the solvent was removed by distillation under a reduced pressure to obtain 2.98 g of crude vitamin A.

To the obtained crude vitamin A, 1.45 g (16.7 mmol) of trimethylacetaldehyde and 86 mg (0.42 mmol) of aluminum isopropoxide were added, and agitated at 40°-45° C. for 50 min. After the stopping of reaction by the addition of 0.07 ml of water, unreacted trimethylacetaldehyde and neopentyl alcohol formed as a reaction by-product were distilled off (at 50° C., 10 mmHg) to obtain 3.36 g of crude vitamin A aldehyde (purity 61.2%, yield 87%, total trans form ratio 98.4%).

The obtained crude vitamin A aldehyde was recrystallized from hexane to obtain 1.45 g of purified vitamin A aldehyde (melting point 60°-61° C.).

EXAMPLE 2

Synthesis of Vitamin A Aldehyde using 2,2-dimethyl-4-pentenal

After the reaction of 2.8 g (8.37 mmol) of vitamin A acetate (purity 98%) with 1.2 g of an aqueous 50% sodium hydroxide solution in 15 g of methanol at room temperature for 1 hour, hexane and water were added to the reaction mixture and the organic layer was separated. After the obtained organic layer was washed with water, the organic solvent was removed by distillation under a reduced pressure to obtain 3.05 g of crude vitamin A.

To the obtained crude vitamin A, 1.86 g (16.5 mmol) of 2,2-dimethyl-4-pentenal and 86 mg (0.42 mmol) of aluminum isopropoxide were added, and the reaction mixture was agitated at 35°-40° C. for 60 min. After the stopping of reaction by the addition of 0.07 ml of water, unreacted 2,2-dimethyl-4-pentenal and 2,2-dimethyl-4-penten-1-ol formed as a reaction by-product were distilled off (at 60° C., 10 mmHg) to obtain 3.77 g of crude vitamin A aldehyde (purity 55.5%, yield 87%, total trans form ratio 98%).

The obtained crude vitamin A aldehyde was recrystallized from hexane to obtain 1.25 g of purified vitamin A aldehyde (melting point 60°-61° C.).

COMPARATIVE EXAMPLE

Vitamin A aldehyde was prepared by the method described in Hawkins, et. al., J. Chem. Soc. 411 (1944).

After the reaction of 0.96 g (2.87 mmol) of vitamin A acetate (purity 98%) with 0.5 g of an aqueous 50% sodium hydroxide solution in 5 g of methanol at room temperature for 1 hour, hexane and water were added to the reaction mixture and the organic layer was separated.

After the obtained organic layer was washed with water, the orgnic solvent was removed by distillation under a reduced pressure to obtain 1.2 g of crude vitamin A.

In a pressure tube having a capacity of 100 ml, the obtained crude vitamin A, 15 ml of acetaldehyde, 2 g of aluminum isopropoxide and 40 ml of benzene were placed and reacted at 65°-70° C. for 48 hours.

After the reaction mixture was cooled and added 30 ml of water, the reaction mixture was vigorously agitated, thereafter solids in the reaction mixture were removed by filteration with Celite.

After the organic layer was separated and washed with an aqueous 1% hydrochloric acid solution and an aqueous 5% sodium hydrogencarbonate solution successively, the organic solvent was removed by distillation under a reduced pressure, to obtain crude vitamin A aldehyde which was found to contain 11.8%, 1.17 mmol of vitamin A aldehyde (yield 39.0%) and 1.8%, 0.17 mmol of vitamin A (recovery 5.9%) by liquid chromatographic analysis.

What is claimed is:

1. A process for producing vitamin A aldehyde which comprises reacting vitamin A with an aldehyde of the formula (1)

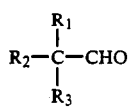

(I)

wherein $R_1$, $R_2$ and $R_3$ are the same or different and each represent a lower alkyl group or a lower alkenyl group, in the presence of a catalytic amount of aluminum alkoxide.

2. A process according to claim 1, wherein the aldehyde is trimethylacetoaldehyde or 2,2-dimethyl-4-pentenal.

3. A process according to claim 1, wherein the aldehyde is used in an amount of 1 or more equivalent relative to vitamin A.

4. A process according to claim 3, wherein the aldehyde is used in an amount of in the range of 1.1–3 equivalents relative to vitamin A.

5. A process according to claim 1, wherein aluminum alkoxide is used in an amount of in the range of 0.1–30 mole percent relative to vitamin A.

6. A process according to claim 1, wherein the reaction is carried out at a temperature in the range of 10°–80° C.

* * * * *